(12) United States Patent
Roh et al.

(10) Patent No.: US 10,034,862 B2
(45) Date of Patent: Jul. 31, 2018

(54) SOLID PHARMACEUTICAL COMPOSITION COMPRISING AMLODIPINE AND LOSARTAN

(71) Applicant: HANMI PHARM. CO., LTD., Hwaseong-si, Gyeonggi-do (KR)

(72) Inventors: Leedong Roh, Anyang-si (KR); Ho Taek Im, Yongin-si (KR); Young Su Yoon, Seoul (KR); Yong Il Kim, Suwon-si (KR); Jae Hyun Park, Suwon-si (KR); Jong Soo Woo, Suwon-si (KR)

(73) Assignee: HANMI PHARM. CO., LTD., Hwaseong-si (KR)

(*) Notice: Subject to any disclaimer, the term of this patent is extended or adjusted under 35 U.S.C. 154(b) by 0 days.

(21) Appl. No.: 15/515,731

(22) PCT Filed: Sep. 1, 2015

(86) PCT No.: PCT/KR2015/009203
§ 371 (c)(1),
(2) Date: Mar. 30, 2017

(87) PCT Pub. No.: WO2016/052866
PCT Pub. Date: Apr. 7, 2016

(65) Prior Publication Data
US 2017/0326110 A1    Nov. 16, 2017

(30) Foreign Application Priority Data
Sep. 30, 2014 (KR) .......... 10-2014-0131834

(51) Int. Cl.
| A61K 31/44 | (2006.01) |
| A61K 31/41 | (2006.01) |
| A61K 31/417 | (2006.01) |
| A61K 31/4178 | (2006.01) |
| A61K 9/20 | (2006.01) |

(52) U.S. Cl.
CPC .......... *A61K 31/417* (2013.01); *A61K 9/2027* (2013.01); *A61K 9/2059* (2013.01); *A61K 9/2077* (2013.01); *A61K 31/4178* (2013.01); *A61K 31/44* (2013.01)

(58) Field of Classification Search
CPC ............................. A61K 31/44; C07D 257/04
USPC ........................................ 514/354, 381, 356
See application file for complete search history.

(56) References Cited

U.S. PATENT DOCUMENTS

| 5,138,069 A | 8/1992 | Carini et al. |
| 5,153,197 A | 10/1992 | Carini et al. |
| 5,608,075 A | 3/1997 | Campbell, Jr. et al. |
| 2011/0206761 A1 | 8/2011 | Naware et al. |
| 2011/0245301 A1* | 10/2011 | Park .................... A61K 9/2013 514/356 |
| 2011/0245302 A1 | 10/2011 | Park et al. |
| 2011/0251245 A1 | 10/2011 | Woo et al. |
| 2014/0227356 A1* | 8/2014 | Kim .................. A61K 31/4178 424/454 |

FOREIGN PATENT DOCUMENTS

| KR | 10-2010-0086921 A | 8/2010 |
| KR | 10-2012-0110163 A | 10/2012 |
| KR | 10-2013-0039797 A | 4/2013 |
| MX | 2011006061 A | 6/2011 |
| WO | 2013/055177 A1 | 4/2013 |
| WO | 2013/100630 A1 | 7/2013 |

OTHER PUBLICATIONS

Written Opinion of the International Searching Authority of PCT/KR2015/009203 dated Oct. 29, 2015.
International Search Report of PCT/KR2015/009203 dated Oct. 29, 2015.

* cited by examiner

*Primary Examiner* — Raymond J Henley, III
(74) *Attorney, Agent, or Firm* — Sughrue Mion, PLLC

(57) ABSTRACT

The present invention provides a pharmaceutical composition for the prevention or treatment of cardiovascular disorders containing losartan or a pharmaceutically acceptable salt thereof; amlodipine or a pharmaceutically acceptable salt thereof; a disintegrant; and a coating agent.

The composition of the present invention, which has the best combination and optimum ratio of a disintegrant to a coating agent, shows sufficient strength and high dissolution rates under various pH environments, and thus, it is useful for the preparation of an excellent solid formulation exhibiting improved drug delivery efficiency and storage stability.

11 Claims, 2 Drawing Sheets

SOLID PHARMACEUTICAL COMPOSITION COMPRISING AMLODIPINE AND LOSARTAN

CROSS REFERENCE TO RELATED APPLICATIONS

This application is a National Stage of International Application No. PCT/KR2015/009203 filed Sep. 1, 2015, claiming priority based on Korean Patent Application No. 10-2014-0131834 filed Sep. 30, 2014, the contents of all of which are incorporated herein by reference in their entirety.

FIELD OF THE INVENTION

The present invention relates to a solid pharmaceutical composition comprising amlodipine and losartan as active ingredients which has improved dissolution rates and storage stability of them.

BACKGROUND OF THE INVENTION

In the treatment of hypertension, it is essential to maintain blood pressure within a normal range rather than just control the symptoms thereof, thereby preventing life-threatening diseases such as stroke, heart failure, and coronary heart diseases (e.g., myocardial infarction), and cardiovascular complications such as renal failure. Since long-term administration of an antihypertensive drug is required for controlling blood pressure, selection of the drug should be made carefully. Further, advanced therapy using a combination of two or more drugs having pharmacological actions different from each other makes it possible to improve preventive or therapeutic effects, while reducing side effects arising from the long-term administration of a drug by lowering the amounts of individual drugs.

Antihypertensive drugs commonly used may be divided into three major categories such as diuretics, sympatholytics and vasodilators based on their action mechanisms. Vasodilators, widely prescribed antihypertensive drugs, may be further divided into several groups such as angiotensin converting enzyme (ACE) inhibitors, angiotensin II receptor blockers and calcium channel blockers based on their pharmacological actions.

Amlodipine is the generic name for 3-ethyl-5-methyl-2-(2-aminoethoxy-methyl)-4-(2-chlorophenyl)-6-methyl-1,4-dihydro-3,5-pyridine dicarboxylate, and amlodipine besylate is currently marketed as Norvasc®. Amlodipine blocks calcium channels, and is used for the treatment of cardiovascular disorders such as angina, hypertension and congestive heart failure.

Losartan is the generic name for 2-butyl-4-chloro-1-[[2'-(1H-tetrazol-5-yl)[1,1'-biphenyl]-4-yl]methyl]-1H-imidazol-5-methanol, which has been disclosed in U.S. Pat. Nos. 5,608,075; 5,138,069; and 5,153,197, etc. Losartan potassium is currently available as Cozaar®. Losartan blocks the binding of angiotensin II, a vasoconstrictor, to its receptor. It is used for treating hypertension, heart failure, ischemic peripheral circulation disorder, myocardial ischemia (angina pectoris), diabetic neuropathy and glaucoma, and also used for preventing the progression of heart failure post-myocardial infarction.

The present inventors found that a combined formulation of amlodipine and losartan having two distinct pharmacological action mechanisms is useful for the treatment of hypertension, and have conducted intensive studies on such a combined formulation. However, when the combined formulation of amlodipine and losartan was prepared, undesirable gelation of losartan was observed. More particularly, losartan is easily dissolved in purified water or at a relatively high pH (e.g., pH 6.8, etc.) showing good dissolution patterns, but it is very slowly dissolved at a low pH (e.g., pH 1.2 or 2.0) because of its gelation. As such, in the combined formulation of amlodipine and losartan, amlodipine may also be trapped in the losartan gel due to the gelation of losartan, resulting in a decrease in dissolution rate.

An oral formulation generally undergoes disintegration and dissolution in stomach, which has low pH contents. Accordingly, a low dissolution rate of an active ingredient at a low pH (e.g., pH 1 or 2) can significantly affect its bioavailability.

In addition, considering that the gastric pH of a normal adult varies widely in a range of 1.0 to 3.5 and Cmax of losartan after food ingestion is reduced by about 10% (PDR), development of a formulation capable of maintaining a relatively constant dissolution rate despite such variations of gastric pH is needed to achieve maximum effect of a drug by maximizing drug absorption and minimizing variations in drug absorption within an individual or among individuals. In this context, in case of a combined formulation of amlodipine and losartan, a high amount of at least one type of disintegrant is required to develop a formulation which shows little differences in dissolution rate at a normal range of gastric pH variations, and shows high dissolution rate by preventing the gelation of losartan under low pH conditions. However, a formulation using a relatively high content of disintegrant may have problems in its storage stability due to the water absorbing property of the disintegrant. More particularly, upon exposure to moisture, a pharmaceutical composition using a high amount of disintegrant is likely to show changes in its property and a decrease in its efficacy. Thus, there has been a need for developing a pharmaceutical composition with improved storage stability, to prevent the decrease in dissolution rate.

The present inventors have therefore endeavored to develop a combined formulation comprising losartan and amlodipine, for the prevention or treatment of cardiovascular disorders, in the form of a solid formulation which has improved dissolution rate, stability and therapeutic efficacy. As a result, the present inventors have found that, by employing a disintegrant and a coating agent in a composition at a specific ratio, low dissolution rate arising from the losartan gelation in an acidic environment can be significantly improved, while changes in the properties of the composition upon exposure to moisture can be prevented, affording efficient delivery of its active ingredients and improved storage stability.

In the present patent application, reference will be made to articles and patent documents along with citations thereto. The contents of the articles and patent documents are herein incorporated by reference in their entireties, and thereby the level of technical field to which the present invention belong and the disclosure of the present invention are explained with more clarity.

SUMMARY OF THE INVENTION

Therefore, it is an object of the present invention to provide a pharmaceutical composition for the prevention or treatment of cardiovascular disorders.

In accordance with one object of the present invention, there is provided a pharmaceutical composition for the prevention or treatment of cardiovascular disorders comprising (A) losartan or a pharmaceutically acceptable salt thereof; (B) amlodipine or a pharmaceutically acceptable salt thereof; (C) a disintegrant in an amount of 3 to 10% by weight based on the total weight of the composition; and (D) a coating agent.

The composition of the present invention, which has the best combination and optimum ratio of a disintegrant to a coating agent, shows sufficient strength and high dissolution rates under various pH environments, and thus, it is useful for the preparation of an excellent solid formulation exhibiting improved drug delivery efficiency and storage stability.

DETAILED DESCRIPTION OF THE INVENTION

Figure 1:
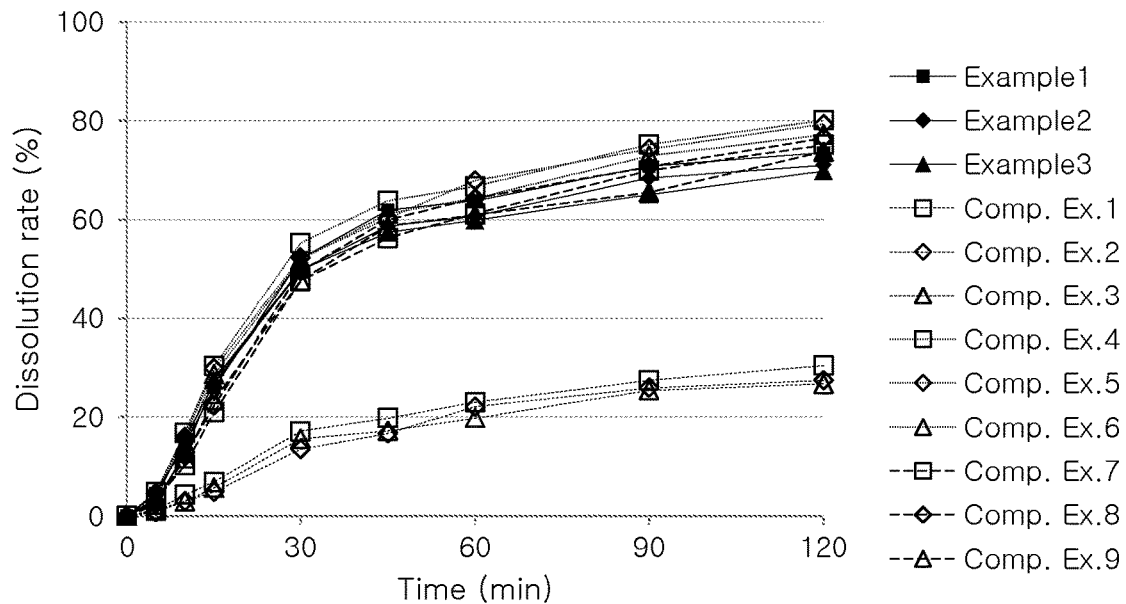
FIG. 1 is a graph showing the dissolution rates of amlodipine of the combined tablets comprising losartan and amlodipine of Examples 1 to 3, and Comparative Examples 1 to 9.

According to one embodiment of the present invention, there is provided a pharmaceutical composition for the prevention or treatment of cardiovascular disorders comprising:

(A) losartan or a pharmaceutically acceptable salt thereof;

(B) amlodipine or a pharmaceutically acceptable salt thereof;

(C) a disintegrant in an amount of 3 to 10% by weight based on the total weight of the composition; and (D) a coating agent.

As used herein, the term "cardiovascular disorder" refers to a disorder caused by increased blood pressure or decreased blood flow to heart muscles due to narrowing or obstruction of a coronary artery that supplies blood to the heart. Specifically, the cardiovascular disorder to be prevented or treated by a composition of the present invention may be selected from the group consisting of angina pectoris, hypertension, arterial vasospasm, cardiac arrhythmia, cardiac hypertrophy, cerebral infarct, congestive heart failure and myocardial infarction.

As used herein, the term "treatment" refers to (a) inhibition of development of a disorder, a disease or a symptom; (b) alleviation of a disorder, a disease or a symptom; or (c) elimination of a disorder, a disease or a symptom. Losartan and amlodipine, pharmacological ingredients employed in the composition of the present invention, inhibit, eliminate or alleviate the development of a cardiovascular disorder or its symptom by blocking angiotensin II receptors and calcium channels, respectively. Therefore, the composition of the present invention itself can be a therapeutic composition for a cardiovascular disorder, and it can also be a therapeutic adjuvant to be co-administered with other pharmacological ingredients to improve the cardiovascular function or blood flow. Thus, as used herein, the term "treatment" or "therapeutics" is intended to include the meaning of "treatment adjuvant" or "therapeutics adjuvant."

As used herein, the term "prevention" refers to inhibition of occurrence of a disorder or a disease in a subject who has not been diagnosed to have a disorder or a disease but has a possibility of developing such disorder or disease.

According to a specific embodiment of the present invention, losartan or a pharmaceutically acceptable salt thereof is employed in an amount of 15 to 30% by weight based on the total weight of the composition. More specifically, it is employed in an amount of 17 to 25% by weight, and most specifically 18 to 22% by weight.

Losartan used in the present invention may be one of the various forms of pharmaceutically acceptable salts. A useful example of the pharmaceutically acceptable salts is an acid addition salt formed by a pharmaceutically acceptable free acid. The free acid may be an organic or inorganic acid.

Examples of pharmaceutically acceptable salts of losartan may include losartan sodium, losartan potassium, losartan strontium, losartan calcium, losartan magnesium, losartan ammonium or a mixture thereof, but are not limited thereto, and any form of salts conventionally used for the preparation of a pharmaceutical composition in the art can be employed. Most specifically, a pharmaceutically acceptable salt of losartan used in the present invention may be losartan potassium.

Based on a unit dosage form (solid administration form), losartan or a pharmaceutically acceptable salt thereof is conventionally employed in an amount of, for example, 10 to 500 mg, specifically 25 to 250 mg, more specifically 50 to 200 mg, and most specifically 50 to 100 mg.

According to a specific embodiment of the present invention, amlodipine or a pharmaceutically acceptable salt thereof is employed in amount of 3 to 20% by weight based on the weight of the losartan or a pharmaceutically acceptable salt thereof. More specifically, it is employed in an amount of 5 to 15% by weight, even more specifically 6 to 12% by weight, and most specifically 7 to 9% by weight.

Amlodipine used in the present invention may be one of the various forms of pharmaceutically acceptable salts. Examples of the pharmaceutically acceptable salts of amlodipine may include chloride, hydrobromide, sulfate, phosphate, acetate, maleate, fumarate, lactate, tartrate, citrate, gluconate, besylate and camsylate salt, but are not limited thereto, and any form of salts formed by various inorganic or organic acids conventionally used in the art can be employed. Specifically, the pharmaceutically acceptable salt of amlodipine may be amlodipine besylate or amlodipine camsylate, and more specifically, amlodipine camsylate. Also, amlodipine, 3-ethyl-5-methyl-2-(2-aminoethoxymethyl)-4-(2-chlorophenyl)-6-methyl-1,4-dihydro-3,5-pyridine dicarboxylate, used in the present invention covers all of its stereoisomers.

Based on a unit dosage form (solid administration form), amlodipine is conventionally employed in an amount of, for example, 1.25 to 20 mg, specifically 1.875 to 15 mg, more specifically 2.5 to 10 mg, and most specifically 5 to 10 mg. The amount of amlodipine described above refers to the amount of free amlodipine present in its solid dosage form.

As used herein, the term "disintegrant" refers to a material that accelerates disintegration of a solid formulation, especially a tablet, by improving its solubility, enabling an active ingredient of the formulation to be dissolved in a therapeutically effective amount. The term "therapeutically effective amount" refers to a sufficient amount of a pharmacological ingredient to provide therapeutic or preventive effect to a subject, which is thus intended to encompass the meaning of "preventively effective amount."

A dissolution delay arising from a disintegration delay may be improved by increasing the amount of a disintegrant, but excessive use of a disintegrant may result in a solid formulation (e.g., a tablet) which fails to show enough strength to maintain its form/property during the preparation, packaging, transportation or storage process. A disintegrant of the present invention may be employed in an amount of 2.5 to 30% by weight based on the total weight of the composition, specifically 3 to 10% by weight, and more specifically 5 to 9% by weight.

According to a specific embodiment of the present invention, a disintegrant employed in the present invention may be at least one selected from the group consisting of sodium starch glycolate, croscarmellose sodium and crospovidone.

As used herein, the term "coating agent" refers to a material that lowers water permeability and improves mechanical strength and storage stability by modifying the surface of a solid formulation to form an outer shell. By employing a disintegrant at a specific ratio in a solid formulation containing amlodipine and losartan as pharmacological ingredients, the dissolution rate of the formulation may be improved but its stability may be worsened upon exposure to moisture. Thus, a coating agent can be additionally employed to increase the strength and stability of the formulation.

As used herein, the term "coating" refers to binding to the surface of a material to be coated (modified) without changing the basic physical property of the material. For example, the expression "the surface of a solid formulation is coated with a coating agent" means that molecules of the coating agent have directly or indirectly bound to a delocalized area of the surface of the solid formulation. Therefore, it would be apparent that "coating," as used herein, is not limited to the cases where a layer, which completely covers the surface of a material to be coated is formed. More specifically, the term "coating," as used herein, refers to binding to the surface of a material, occupying enough surface area to obtain desired strength and stability.

According to a specific embodiment of the present invention, the coating agent is employed in an amount of 1 to 10% by weight based on the total weight of the composition, more specifically 1 to 5% by weight, and most specifically 2 to 4% by weight.

According to a specific embodiment of the invention, the coating agent employed in the present invention is at least one polymer selected from the group consisting of a coating agent containing polyvinyl alcohol (for example, Opadry), hypromellose, and hydroxypropyl cellulose.

According to a specific embodiment of the invention, the hypromellose has a viscosity of 10 to 30 mPa·s, more specifically 10 to 20 mPa·s, and even more specifically 10 to 15 mPa·s. According to the present invention, it was observed that storage stability decreased upon exposure to moisture if the viscosity of the coating agent was less than 10 mPa·s.

According to a specific embodiment of the present invention, the weight ratio of the disintegrant to the coating agent in the composition ranges from 1.5:1 to 4.0:1. According to the present invention, with regard to a solid formulation which employs amlodipine and losartan as pharmacological ingredients, the dissolution of the pharmacological ingredients can be improved by employing a disintegrant, and also, declining of strength, stability, and preservability of the formulation can be prevented by employing a coating agent. Therefore, the ratio between these two ingredients which play complementary roles to each other is important to achieve efficient drug delivery and drug stability. More specifically, the weight ratio of the disintegrant to the coating agent in the composition of the present invention may be in the range of 1.9:1 to 3.0:1, even more specifically 2.2:1 to 3.0:1, and most specifically 2.2:1 to 2.5:1.

According to a specific embodiment of the present invention, the composition of the present invention can be formulated into a coated tablet which shows a thickness increase of 3% or less upon exposure to accelerated conditions of 40° C. and 75% relative humidity for 5 hours.

According to a specific embodiment of the present invention, the composition of the present invention can be formulated into a coated tablet which shows a mass increase of 5% or less upon exposure to accelerated conditions of 40° C. and 75% relative humidity for 5 hours.

According to the present invention, a solid formulation prepared by using a composition of the present invention shows a thickness increase and a mass increase of 3% or less and 5% or less, respectively, upon exposure to a high humidity environment of 75% relative humidity since water absorption is blocked, thereby achieving excellent storage stability.

As such, owing to the best combination and optimum ratio of the disintegrant to the coating agent, a solid formulation prepared by using the composition of the present invention shows excellent dissolution rate and storage stability.

The composition of the present invention may be formulated into various forms of solid formulations such as, for example, a tablet, a capsule or multi-particles, and may be administered by various routes such as, for example, oral, peroral or hypoglossal route. Specifically, a composition of the present invention may be formulated into a tablet and orally administered. Ingredients of the composition of the present invention other than the coating agent may be simply mixed and tableted to obtain a plain tablet, which may be coated with the coating agent to obtain a final tablet. A tablet requires an appropriate hardness, and average hardness in the rage of 5 kp to 30 kp is preferable. Measurement of the average hardness is carried out before applying a coating layer onto the tablet.

Hereinafter, the present invention is explained in detail by Examples. The following Examples are intended to further illustrate the present invention without limiting its scope.

EXAMPLES

Examples 1 to 3 and Comparative Examples 1 to 9

Preparation of Combined Tablets I

Example 1

| -Wet granule part- | |
|---|---|
| amlodipine camsylate | 7.84 mg (amlodipine 5 mg) |
| butylated hydroxytoluene (BHT) | 0.1 mg |
| mannitol | 27 mg |
| microcrystalline cellulose | 61 mg |
| sodium starch glycolate | 17 mg |
| polyvinylpyrrolidone | 3.2 mg |

-continued

| -Roller compacting part- | |
|---|---|
| losartan potassium | 100 mg |
| microcrystalline cellulose | 260 mg |
| crospovidone | 18 mg |
| -Final mixing part- | |
| magnesium stearate | 3.2 mg |
| -Coating agent- | |
| talc | 0.25 mg |
| titanium oxide | 2.25 mg |
| hydroxypropyl cellulose | 2.5 mg |
| hypromellose (15 mPa · s) | 10 mg |
| ethanol | 325 mg |
| purified water | 85 mg |

*Ethanol and purified water are evaporated during a coating process.

According to the compositions as above, amlodipine camsylate, butylated hydroxytoluene, mannitol, microcrystalline cellulose, and sodium starch glycolate were put into a high speed mixer; allowed to unite for 7 minutes while supplying polyvinylpyrrolidone dissolved in an appropriate amount of water to the high speed mixer as a binder solution; and dried for 30 minutes using a fluid bed dryer. The dried materials thus obtained were sized using Fitz Mill to prepare wet granules. Also, dry granules were prepared by mixing losartan potassium, microcrystalline cellulose and crospovidone, which were then subjected to compacting process using a roller compactor.

The wet and dry granules were mixed, and then lubricated by mixing with magnesium stearate, a final mixing part. The resulting mixture was tableted with a compression force of about 20 kN using a rotary tablet press (Sejong Pharmatech, MRC-45) to prepare a losartan 100 mg-amlodipine 5 mg combined tablet. After preparing a coating solution according to the specified coating compositions the combined tablet was film-coated with an inflowing air temperature of 50° C. and outflowing air temperature of 40° C. using an automatic coating device (Sejong Pharmatech, SFC-30), and the resulting tablet was dried at 35° C. for 30 minutes to prepare a film-coated tablet.

Example 2

| -Wet granule part, roller compacting part and final mixing part- | |
|---|---|
| same as Example 1 | |
| -Coating agent- | |
| Opadry 85f18422 (polyvinyl alcohol 40%, titanium oxide 25%, polyethylene glycol 20.2%, and talc 14.8%) | 15 mg |
| purified water | 100 mg |

*Purified water is evaporated during a coating process.

A combined tablet was prepared by repeating the procedure of Example 1.

Example 3

| -Wet granule part, roller compacting part and final mixing part- | |
|---|---|
| same as Example 1 | |
| -Coating agent- | |
| Opadry 80W AMB (polyvinyl alcohol 40~50%, titanium oxide 20~30%, talc about 20%, lecithin about 2%, Xanthan Gum about 1%) | 15 mg |
| purified water | 100 mg |

*Purified water is evaporated during a coating process.

A combined tablet was prepared by repeating the procedure of Example 1.

Comparative Example 1

| -Wet granule part- | |
|---|---|
| amlodipine camsylate | 7.84 mg (amlodipine 5 mg) |
| butylated hydroxytoluene | 0.1 mg |
| mannitol | 27 mg |
| microcrystalline cellulose | 61 mg |
| sodium starch glycolate | 6 mg |
| polyvinylpyrrolidone | 3.2 mg |
| -Roller compacting part- | |
| losartan potassium | 100 mg |
| microcrystalline cellulose | 260 mg |
| crospovidone | 6 mg |
| -Final mixing part- | |
| magnesium stearate | 3.2 mg |
| -Coating agent- | |
| same as Example 1 | |

A combined tablet was prepared by repeating the procedure of Example 1.

Comparative Example 2

—Wet Granule Part, Roller Compacting Part and Final Mixing Part—same as Comparative Example 1
—Coating Agent—same as Example 2
A combined tablet was prepared by repeating the procedure of Example 1.

Comparative Example 3

—Wet Granule Part, Roller Compacting Part and Final Mixing Part—
same as Comparative Example 1
—Coating Agent—
same as Example 3
A combined tablet was prepared by repeating the procedure of Example 1.

Comparative Example 4

| -Wet granule part- | |
|---|---|
| amlodipine camsylate | 7.84 mg (amlodipine 5 mg) |
| butylated hydroxytoluene | 0.1 mg |

-continued

| | |
|---|---|
| mannitol | 27 mg |
| microcrystalline cellulose | 61 mg |
| sodium starch glycolate | 30 mg |
| polyvinylpyrrolidone | 3.2 mg |
| -Roller Compacting part- | |
| losartan potassium | 100 mg |
| microcrystalline cellulose | 260 mg |
| crospovidone | 30 mg |
| -Final mixing part- | |
| magnesium stearate | 3.2 mg |
| -Coating agent- | |
| same as Example 1 | |

A combined tablet was prepared by repeating the procedure of Example 1.

Comparative Example 5

—Wet Granule Part, Roller Compacting Part and Final Mixing Part—
same as Comparative Example 4
—Coating Agent—
same as Example 2
A combined tablet was prepared by repeating the procedure of Example 1.

Comparative Example 6

—Wet Granule Part, Roller Compacting Part and Final Mixing Part—
same as Comparative Example 4
—Coating Agent—
same as Example 3
A combined tablet was prepared by repeating the procedure of Example 1.

Comparative Example 7

| | |
|---|---|
| -Wet granule part, roller compacting part and final mixing part- | |
| same as Example 1 | |
| -Coating agent- | |
| talc | 0.25 mg |
| titanium oxide | 2.25 mg |
| hydroxypropyl cellulose | 2.5 mg |
| hypromellose (3 mPa · s) | 10 mg |
| ethanol | 325 mg |
| purified water | 85 mg |

*Ethanol and purified water are evaporated during a coating process.

A combined tablet was prepared by repeating the procedure of Example 1.

Comparative Example 8

| | |
|---|---|
| -Wet granule part, roller compacting part and final mixing part- | |
| same as Example 1 | |
| -Coating agent- | |
| talc | 0.25 mg |
| titanium oxide | 2.25 mg |
| hydroxypropyl cellulose | 2.5 mg |
| hypromellose (4.5 mPa · s) | 10 mg |
| ethanol | 325 mg |
| purified water | 85 mg |

* Ethanol and purified water are evaporated during a coating process.

A combined tablet was prepared by repeating the procedure of Example 1.

Comparative Example 9

| | |
|---|---|
| -Wet granule part, roller compacting part and final mixing part- | |
| same as Example 1 | |
| -Coating agent- | |
| talc | 0.25 mg |
| titanium oxide | 2.25 mg |
| hydroxypropyl cellulose | 2.5 mg |
| hypromellose (6 mPa · s) | 10 mg |
| ethanol | 325 mg |
| purified water | 85 mg |

*Ethanol and purified water are evaporated during a coating process.

A combined tablet was prepared by repeating the procedure of Example 1.

The compositions of combined formulations prepared in Examples 1 to 3 and Comparative Examples 1 to 9 are shown in Table 1 below.

TABLE 1

| | Composition | Ex. 1 | Ex. 2 | Ex. 3 | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 |
|---|---|---|---|---|---|---|---|---|---|---|---|---|---|
| | Disintegrant ratio (%) | 6.8 | 6.8 | 6.8 | 2.5 | 2.5 | 2.5 | 11.2 | 11.2 | 11.2 | 6.8 | 6.8 | 6.8 |
| Wet granule | Amlodipine camsylate | 7.84 | 7.84 | 7.84 | 7.84 | 7.84 | 7.84 | 7.84 | 7.84 | 7.84 | 7.84 | 7.84 | 7.84 |
| | BHT | 0.1 | 0.1 | 0.1 | 0.1 | 0.1 | 0.1 | 0.1 | 0.1 | 0.1 | 0.1 | 0.1 | 0.1 |
| | Mannitol | 27 | 27 | 27 | 27 | 27 | 27 | 27 | 27 | 27 | 27 | 27 | 27 |
| | Microcrystalline cellulose | 61 | 61 | 61 | 61 | 61 | 61 | 61 | 61 | 61 | 61 | 61 | 61 |
| | Sodium starch glycolate | 17 | 17 | 17 | 6 | 6 | 6 | 30 | 30 | 30 | 17 | 17 | 17 |
| | Poly-vinylpyrrolidone | 3.2 | 3.2 | 3.2 | 3.2 | 3.2 | 3.2 | 3.2 | 3.2 | 3.2 | 3.2 | 3.2 | 3.2 |

TABLE 1-continued

| Composition | | Ex. 1 | Ex. 2 | Ex. 3 | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 |
|---|---|---|---|---|---|---|---|---|---|---|---|---|---|
| Roller compacting | Losartan potassium | 100 | 100 | 100 | 100 | 100 | 100 | 100 | 100 | 100 | 100 | 100 | 100 |
| | Microcrystalline cellulose | 260 | 260 | 260 | 260 | 260 | 260 | 260 | 260 | 260 | 260 | 260 | 260 |
| | Crospovidone | 18 | 18 | 18 | 6 | 6 | 6 | 30 | 30 | 30 | 18 | 18 | 18 |
| Final Mixing | Magnesium stearate | 3.2 | 3.2 | 3.2 | 3.2 | 3.2 | 3.2 | 3.2 | 3.2 | 3.2 | 3.2 | 3.2 | 3.2 |
| Coating agent | Talc | 0.25 | — | — | 0.25 | — | — | 0.25 | — | — | 0.25 | 0.25 | 0.25 |
| | Titanium oxide | 2.25 | — | — | 2.25 | — | — | 2.25 | — | — | 2.25 | 2.25 | 2.25 |
| | Hydroxypropyl cellulose | 2.5 | — | — | 2.5 | — | — | 2.5 | — | — | 2.5 | 2.5 | 2.5 |
| | Hypromellose (15 mPa · s) | 10 | — | — | 10 | — | — | 10 | — | — | — | — | — |
| | Hypromellose (3 mPa · s) | — | — | — | — | — | — | — | — | — | 10 | — | — |
| | Hypromellose (4.5 mPa · s) | — | — | — | — | — | — | — | — | — | — | 10 | — |
| | Hypromellose (6 mPa · s) | — | — | — | — | — | — | — | — | — | — | — | 10 |
| | Opadry 85F18422 | — | 15 | — | — | 15 | — | — | 15 | — | — | — | — |
| | Opadry 80W AMB | — | — | 15 | — | — | 15 | — | — | 15 | — | — | — |
| | Total weight (mg/tablet) | 512.3 | 512.3 | 512.3 | 489.3 | 489.3 | 489.3 | 537.3 | 537.3 | 537.3 | 512.3 | 512.3 | 512.3 |

Test Example 1

Amlodipine Dissolution Test

Combined tablets of losartan potassium and amlodipine obtained in Examples 1 to 3 and Comparative Examples 1 to 9 were subjected to an amlodipine dissolution test under the following conditions. The results are shown in FIG. 1.
—Dissolution conditions—
Eluent: artificial gastric juice (pH 1.2) 900 mL
Method (apparatus): USP paddle method, 50 rpm
Temperature: 37° C.
—Analysis conditions—
Column: stainless steel column (inner diameter: 4.6 mm, length: 15 cm) packed with octadecylsilyl-silica gel for liquid chromatography (diameter of 5 μm)
Mobile phase: methanol:0.03M potassium dihydrogen phosphate solution (600:400, v/v)
Detector: ultraviolet spectrophotometer (wavelength 350 nm)
Flow rate: 1.5 mL/min.
Injection volume: 20 μL As a result, Examples 1, 2 and 3 and Comparative Examples 4 to 9, in which the disintegrant ratio, or the ratio of a disintegrant to a composition, was 6.0% or higher, showed excellent dissolution rates of amlodipine, whereas Comparative Examples 1, 2 and 3, in which the disintegrant ratio was less than 3.0%, showed low dissolution rates (see FIG. 1).

Test Example 2

Losartan Potassium Dissolution Test

Figure 2:
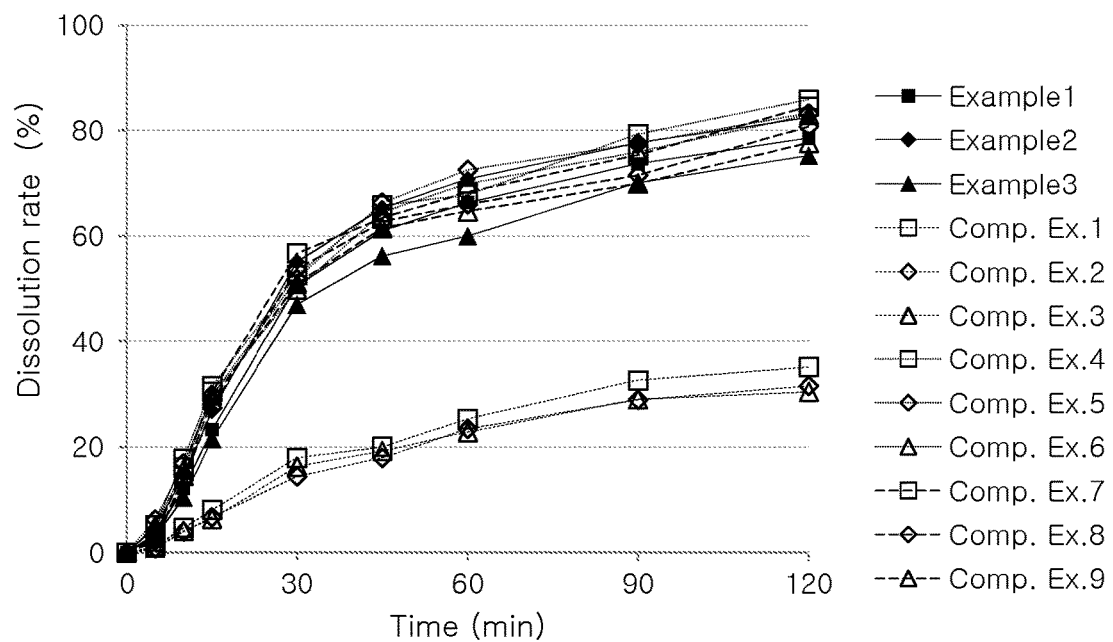
FIG. 2 is a graph showing the dissolution rates of losartan potassium of the combined tablets comprising losartan and amlodipine of Examples 1 to 3 and Comparative Examples 1 to 9.

Combined tablets of losartan potassium and amlodipine obtained in Examples 1 to 3 and Comparative Examples 1 to 9 were subjected to a losartan potassium dissolution test under the following conditions. The results are shown in FIG. 2.
—Dissolution conditions—
Eluent: artificial gastric juice (pH 1.2), 900 mL
Method (apparatus): USP paddle method, 50 rpm
Temperature: 37° C.
—Analysis conditions—
Column: stainless steel column (inner diameter: 4.6 mm, length: 15 cm) packed with octadecylsilyl-silica gel for liquid chromatography (diameter of 5 μm)
Mobile phase:
mobile phase A—phosphate buffer: acetonitrile (850:150, v/v)
mobile phase B—acetonitrile

TABLE 2

| Gradient system | | |
|---|---|---|
| Time (min) | Mobile Phase A % | Mobile Phase B % |
| 0 | 80 | 20 |
| 10 | 40 | 60 |
| 11 | 80 | 20 |
| 15 | 80 | 20 |

Detector: ultraviolet spectrophotometer (wavelength 250 nm)
Flow rate: 1.5 mL/min
Injection volume: 10 μL As a result, Examples 1, 2 and 3 and Comparative Examples 4 to 9, in which the ratio of a disintegrant was 6.0% or higher, showed excellent dissolution rates of losartan potassium, whereas Comparative Examples 1, 2 and 3, in which the disintegrant ratio was less than 3.0%, showed low dissolution rates (see FIG. 2).

Test Example 3

Moisture Exposure Test

Combined tablets of losartan potassium and amlodipine obtained in Examples 1 to 3 and Comparative Examples 4 to 9 were subjected to a moisture exposure test under the following conditions. The results are shown in Table 3 below.

TABLE 3

Results of a moisture exposure test for the coated tablets of Examples 1 to 3 and Comparative Examples 4 to 9.

| | | Ex. 1 | Ex. 2 | Ex. 3 | Comp. Ex. 4 | Comp. Ex. 5 | Comp. Ex. 6 | Comp. Ex. 7 | Comp. Ex. 8 | Comp. Ex. 9 |
|---|---|---|---|---|---|---|---|---|---|---|
| 40° C. 75% 5 h exposure | Mass increase (%) | 2.7 | 1.4 | 0.8 | 6.9 | 6.5 | 4.8 | 6.0 | 4.9 | 4.3 |
| | Thickness increase (%) | 1.6 | 0.9 | 0.5 | 4.1 | 3.7 | 3.5 | 3.5 | 3.0 | 2.7 |
| 50° C. 75% 5 h exposure | Mass increase (%) | 3.8 | 2.7 | 2.0 | 7.2 | 7.0 | 6.9 | 6.7 | 5.7 | 5.2 |
| | Thickness increase (%) | 2.5 | 1.9 | 1.2 | 4.7 | 4.2 | 4.0 | 4.0 | 3.4 | 3.1 |
| 40° C. 75% 24 h exposure | No. of ruptured tablets out of 10 tablets | 0 | 0 | 0 | 7 | 7 | 6 | 6 | 5 | 4 |
| 50° C. 75% 24 h exposure | No. of ruptured tablets out of 10 tablets | 0 | 0 | 0 | 9 | 8 | 8 | 8 | 8 | 6 |

The coated tablets of Examples 1 to 3, which employed at least one type of to high molecular compound selected from the group consisting of polyvinyl alcohol, hypromellose (viscosity: 10 mPa·s or higher), and hydroxypropyl cellulose as a coating agent, showed excellent storage stability. In contrast, the coated tablets of Comparative Examples 7 to 9, which employed two types of high molecular compound as a coating agent, hypromellose (viscosity: 10 mPa·s or less) and hydroxypropyl cellulose, showed poor storage stability upon exposure to moisture as compared to Examples 1 to 3. Meanwhile, the coated tablets of Comparative Examples 4 to 6, as compared to Examples 1 to 3, had the same compositions of coating agents, but the disintegrant ratio was 11.2% which is higher by about 65%, and thus the thickness increase, mass increase and the number of damaged tablets were much higher upon exposure to moisture.

Test Example 4

Accelerated Stability Test

Based on the results of Test Examples 1 to 3, the combined tablets of losartan potassium and amlodipine prepared in Examples 1 to 3, which showed good dissolution rates and storage stability upon exposure to moisture, were subjected to a stability test under accelerated conditions described below. The results are shown in Table 4 below.

<Accelerated Storage Chamber Conditions>
(1) Temperature: 50° C.±2° C.
(2) Package: HDPE bottle packaging
Test timings—Initial and after 28 days of storage
Analysis conditions
Amlodipine related substance: same as the analysis conditions of Test Example 1.
Losartan related substance: same as the analysis conditions of Test Example 2.

TABLE 4

| | Initial | | 50° C., HDPE bottle packaging, 28 days of storage | |
|---|---|---|---|---|
| Sample | Amlodipine related substances (%) | Losartan related substances (%) | Amlodipine related substances (%) | Losartan related substances (%) |
| Ex. 1 | 0.02 | 0.01 | 0.04 | 0.03 |
| Ex. 2 | 0.01 | 0.02 | 0.11 | 0.09 |
| Ex. 3 | 0.03 | 0.01 | 0.12 | 0.13 |

As shown in Table 4, the amounts of related substance production were within allowable ranges in Examples 1 to 3. But the tablets of Examples 2 and 3, in which polyvinyl alcohol was employed, showed higher increases in the production of related substances as compared to the coated tablets of Example 1, in which hypromellose was employed as a coating agent.

The results of Test Examples 1 to 4 indicated that that among the compositions of a coating agent specified for Examples 1 to 3 and Comparative Examples 1 to 9, such as hypromellose with various viscosities and Opadry 58F18422 and 80W AMB which contain polyvinyl alcohol, most preferable was hypromellose with a viscosity of 15 mPa·s, which allowed Example 1 to show the best storage stability upon exposure to moisture and best stability under accelerated conditions.

Examples 4 and 5, and Comparative Examples 10 to 13

Preparation of Combined Formulations II

Combined formulations were prepared according to the compositions of the wet granule part, roller compacting part and final mixing part which were the same as Example 1. Also, they were prepared according to the compositions of the coating agent as shown in Table 5 below, in which the same constituents were employed as Example 1, but the amount of each constituent was either increased or decreased by a specific ratio relative to Example 1.

TABLE 5

Composition of combined formulations of Examples 4 and 5, and Comparative Examples 10 to 13

| Composition | | Comp. Ex. 10 | Comp. Ex. 11 | Comp. Ex. 12 | Ex. 4 | Ex. 5 | Comp. Ex. 13 |
|---|---|---|---|---|---|---|---|
| Coating agent | Talc | — | 0.1 | 0.15 | 0.2 | 0.3 | 0.4 |
| | Titanium oxide | — | 0.9 | 1.35 | 1.8 | 2.7 | 3.6 |
| | Hydroxypropyl cellulose | — | 1.0 | 1.5 | 2.0 | 3.0 | 4.0 |
| | Hypromellose (15 mPa · s) | — | 4.0 | 6.0 | 8.0 | 12.0 | 16.0 |
| | Coating agent | 0 | 6.0 | 9.0 | 12.0 | 18.0 | 24.0 |
| | Total weight (mg/tablet) | 497.3 | 503.3 | 506.3 | 509.3 | 515.3 | 521.3 |

TABLE 6

The disintegrant to coating agent ratios in combined formulations of Examples 1, 4 and 5, and Comparative Examples 10 to 13.

| | Comp. Ex. 10 | Comp. Ex. 11 | Comp. Ex. 12 | Ex. 4 | Ex. 1 | Ex. 5 | Comp. Ex. 13 |
|---|---|---|---|---|---|---|---|
| Mass of disintegrant (mg) | 35 | 35 | 35 | 35 | 35 | 35 | 35 |
| Mass of coating agent (mg) | 0 | 6 | 9 | 12 | 15 | 18 | 24 |
| Disintegrant:coating agent ratio | — | 5.8:1 | 3.9:1 | 2.9:1 | 2.3:1 | 1.9:1 | 1.5:1 |

Test Example 5

Moisture Exposure Test

The tablets of Examples 1, 4 and 5, and Comparative Examples 10 to 13 were subjected to a moisture exposure test by repeating the procedure of Test Example 4. The results are shown in table 7.

TABLE 7

Results of moisture exposure test for combined formulations of Examples 1, 4 and 5, and Comparative Examples 10 to 13.

| | | Comp. Ex. 10 | Comp. Ex. 11 | Comp. Ex. 12 | Ex. 4 | Ex. 1 | Ex. 5 | Comp. Ex. 13 |
|---|---|---|---|---|---|---|---|---|
| 40° C. 75% 5 h exposure | Mass increase (%) | 5.2 | 4.6 | 4.3 | 3.0 | 2.7 | 2.2 | 1.5 |
| | Thickness increase (%) | 3.6 | 2.9 | 2.7 | 1.9 | 1.6 | 1.3 | 1.1 |
| 50° C. 75% 5 h exposure | Mass increase (%) | 6.8 | 5.3 | 5.1 | 4.1 | 3.8 | 2.5 | 1.7 |
| | Thickness increase (%) | 4.1 | 3.3 | 3.2 | 2.7 | 2.5 | 1.5 | 1.3 |
| 40° C. 75% 24 h exposure | Number of ruptured tablets out of 10 tablets | — | 4 | 3 | 0 | 0 | 0 | 0 |
| 50° C. 75% 24 h exposure | Number of ruptured tablets out of 10 tablets | — | 6 | 5 | 0 | 0 | 0 | 0 |

The coated tablets of Examples 1, 4 and 5, and Comparative Example 13, in which the disintegrant to coating agent ratio was 3.0:1 or lower, showed good storage stability, but the plain tablets of Comparative Example 10 and the coated tablets of Comparative Examples 11 and 12, in which the disintegrant to coating agent ratio was 3.9:1 or higher, showed a mass increase and a thickness increase of 5.0% or more and 3.0% or more, respectively. Especially, as for the tablets having the disintegrant to coating tablet disintegrant of 3.9:1 or higher as in the case with coated tablets of Comparative Examples 11 and 12, the higher the ratio, the more tablets became swollen and ruptured, exhibiting their poor storage stability.

Test Example 6

Amlodipine Dissolution Test

Figure 3:
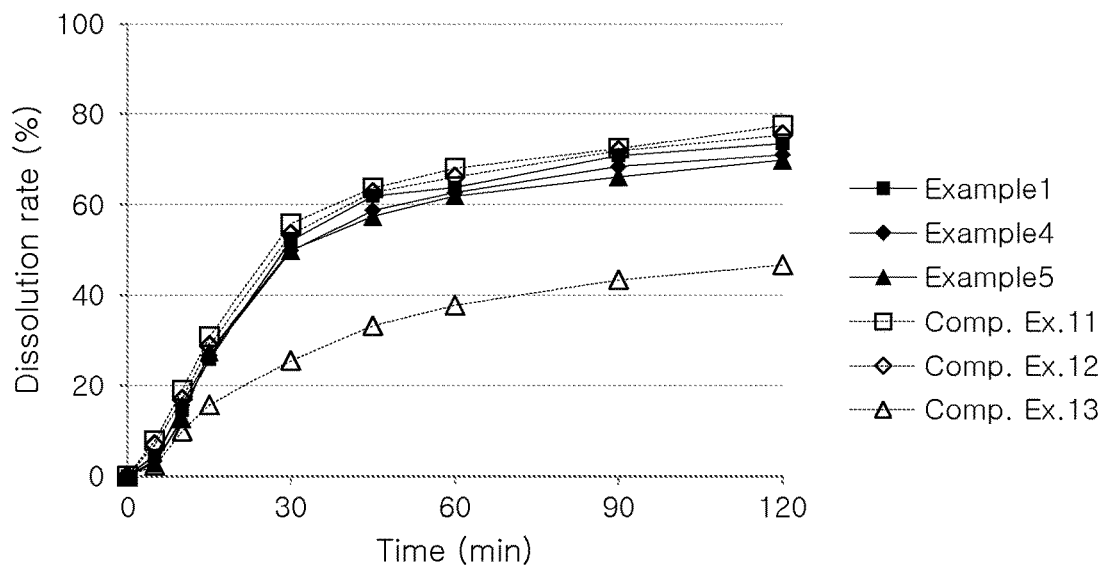
FIG. 3 is a graph showing the dissolution rates of amlodipine of the combined tablets comprising losartan and amlodipine of Examples 1, 4 and 5, and Comparative Examples 11 to 13.

Tablets of Examples 1, 4 and 5 and Comparative Examples 11 to 13 were subjected to a dissolution test by repeating the procedure of Test Example 1. As a result, Examples 1, 4 and 5 and Comparative Examples 11 and 12, in which the disintegrant to coating agent ratio was 1.9:1 or higher, showed high dissolution rates, whereas Comparative Example 13, in which the disintegrant to coating agent ratio was 1.5:1, showed low dissolution rate (see FIG. 3).

Test Example 7

Losartan Potassium Dissolution Test

Figure 4:
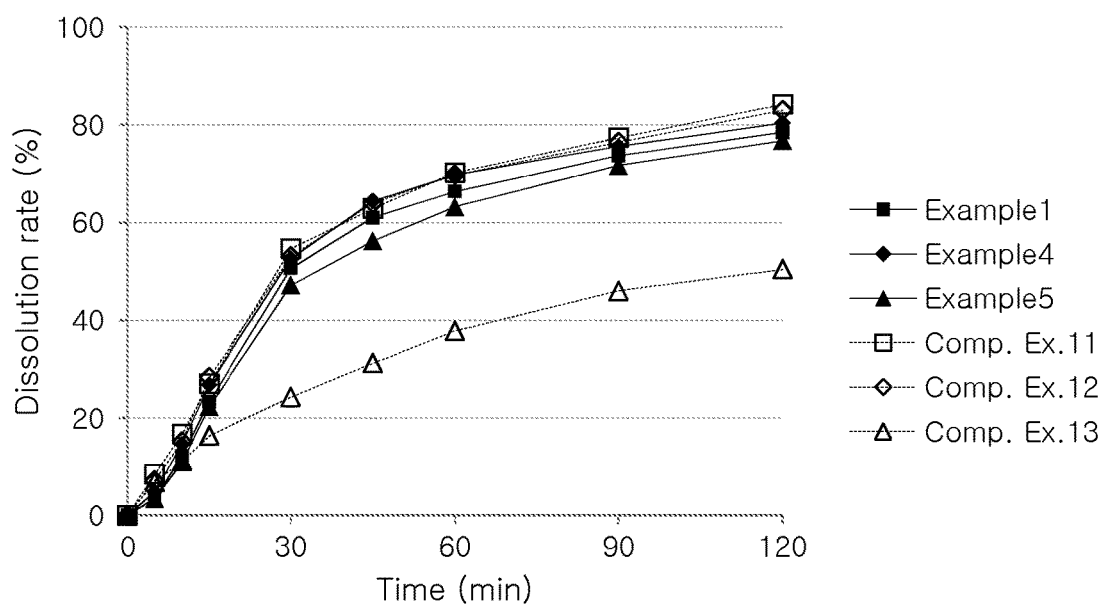
FIG. 4 is a graph showing the dissolution rates of losartan potassium of the combined tablets comprising losartan and amlodipine of Examples 1, 4 and 5, and Comparative Examples 11 to 13.

Tablets of Examples 1, 4 and 5 and Comparative Examples 11 to 13 were subjected to a dissolution test by repeating the procedure of Test Example 2. As a result, Examples 1, 4 and 5 and Comparative Examples 11 and 12, in which the disintegrant to coating agent ratio was 1.9:1 or higher, showed high dissolution rates, whereas Comparative Example 13, in which the disintegrant to coating agent ratio was 1.5:1, showed low dissolution rate (see FIG. 4).

The results of Test Examples 5 to 7 indicated that the coated tablets of Examples 1, 4 and 5, in which the disintegrant to coating agent ratio ranged from about 1.9:1 to about 2.9:1, showed the best storage stability upon moisture exposure and best dissolution rates of amlodipine and losartan potassium.

What is claimed is:

1. A pharmaceutical composition comprising:
   (A) losartan or a pharmaceutically acceptable salt thereof;
   (B) amlodipine or a pharmaceutically acceptable salt thereof;
   (C) a disintegrant in an amount of 3 to 10% by weight based on the total weight of the composition; and
   (D) a coating agent,
   wherein the disintegrant is at least one selected from the group consisting of sodium starch glycolate, croscarmellose sodium and crospovidone;
   wherein the coating agent comprises hypromellose having a viscosity of 10 to 30 mPa·s, and is contained in an amount of 1 to 10% by weight based on the total weight of the composition;
   wherein the weight ratio of the disintegrant to the coating agent in the composition ranges from 1.5:1 to 4.0:1; and
   wherein the composition is in form of a coated tablet which shows a thickness increase of 3% or less upon exposure for 5 hours to conditions of 40° C. and 75% relative humidity and shows a mass increase of 5% or less upon exposure for 5 hours to conditions of 40° C. and 75% relative humidity.

2. The composition of claim 1, wherein the losartan or the pharmaceutically acceptable salt thereof is contained in an amount of 15 to 30% by weight based on the total weight of the composition.

3. The composition of claim 1, wherein the amlodipine or the pharmaceutically acceptable salt thereof is contained in an amount of 3 to 20% by weight based on the weight of the losartan or the pharmaceutically acceptable salt thereof.

4. The composition of claim 1, wherein the amlodipine or the pharmaceutically acceptable salt thereof is contained in an amount of 5 to 15% by weight based on the weight of the losartan or the pharmaceutically acceptable salt thereof.

5. The composition of claim 2, wherein the amlodipine or the pharmaceutically acceptable salt thereof is contained in an amount of 5 to 15% by weight based on the weight of the losartan or the pharmaceutically acceptable salt thereof.

6. The composition of claim 1, wherein the disintegrant is contained in an amount of 5 to 9% by weight based on the total weight of the composition.

7. The composition of claim 1, wherein the coating agent is contained in an amount of 2 to 4% by weight based on the total weight of the composition.

8. The composition of claim 1, wherein the coating agent further comprises at least one selected from the group consisting of polyvinyl alcohol and hydroxypropyl cellulose.

9. The composition of claim 1, wherein the weight ratio of the disintegrant to the coating agent in the composition ranges from 1.9:1 to 3.0:1.

10. The composition of claim 6, wherein the weight ratio of the disintegrant to the coating agent in the composition ranges from 1.9:1 to 3.0:1.

11. A method for inhibition or treatment of a cardiovascular disorder comprising administration of the composition of claim 1, wherein the cardiovascular disorder is selected from the group consisting of angina pectoris, hypertension, arterial vasospasm, cardiac arrhythmia, cardiac hypertrophy, cerebral infarct, congestive heart failure and myocardial infarction.

* * * * *